US00PP24776P2

(12) United States Plant Patent
Zaiger et al.

(10) Patent No.: US PP24,776 P2
(45) Date of Patent: Aug. 19, 2014

(54) CHERRY TREE NAMED 'ROYAL LYDIA'

(50) Latin Name: *Prunus avium*
Varietal Denomination: Royal Lydia

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 40 days.

(21) Appl. No.: 13/815,208

(22) Filed: Feb. 11, 2013

(51) Int. Cl.
*A01H 5/00* (2006.01)

(52) U.S. Cl.
USPC ..... Plt./181

(58) Field of Classification Search
USPC ..... Plt./181
See application file for complete search history.

*Primary Examiner* — Annette Para

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Tree having a low winter chilling requirement.
3. Heavy and regular production of large size fruit.
4. Fruit with good flavor and eating quality.
5. Fruit with good handling and shipping quality.

1 Drawing Sheet

Botanical designation: *Prunus avium.*
Variety denomination: 'ROYAL LYDIA'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Lee' Cherry (U.S. Plant Pat. No. 12,417), 'Royal Tioga' Cherry (U.S. Plant Pat. No. 22,779), 'Bing' Cherry (non-patented) and 'Earlisweet' Cherry (U.S. Plant Pat. No. 9,783), and our proprietary cherry seedling selection '48.5GG273' (non-patented).

STATEMENT REGARDING FEDERALLY SPONSORED RESEARCH AND DEVELOPMENT

Not applicable.

ORIGIN OF THE VARIETY

The present new variety of cherry tree (*Prunus avium*) was developed by us in our experimental orchard located near Modesto, Calif. The new cherry tree originated from a first generation cross between our selected proprietary cherry seedling '48.5GG273' (non-patented) and 'Royal Lee' Cherry (U.S. Plant Pat. No. 12,417). The seed parent (48.5GG273) originated from a second generation cross between 'Bing' Cherry (non-patented) and 'Earlisweet' Cherry (U.S. Plant Pat. No. 9,783). A large number of these first generation seedlings were budded on established trees of 'Mahaleb' Rootstock (non-patented) to accelerate fruit production. Under close and careful observation the present seedling exhibited desirable fruit and tree characteristics and was selected in 2000 for additional asexual propagations and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree is of large size, vigorous, upright growth and has a low winter chilling requirement of approximately 500 hours at or below 45° F. The tree is a regular and productive bearer of large size fruit that has an attractive red skin color. The fruit is further characterized by its good flavor and eating quality, firm flesh with good handling and shipping quality. In comparison to its seed parent (48.5GG273) cherry non-patented the fruit is larger in size and is approximately 7 days later in maturity. In comparison to its pollen parent 'Royal Lee' Cherry (U.S. Plant Pat. No. 12,417) the fruit is larger in size and is approximately 7 days later in maturity. In comparison to the commercial variety 'Royal Tioga' Cherry (U.S. Plant Pat. No. 22,779) the fruit of the new variety is larger in size and is approximately 13 days later in maturity.

DESCRIPTION OF THE PHOTOGRAPH

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 12 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 12 year old specimens grown near Modesto, Calif., with color in accordance with Munsell Book of Color published in 1958.

Tree:

*Size*.—Large. Tree pruned to 3 to 4 meters in height and width for economical harvesting of fruit. Varies with different cultural practices.

*Vigor*.—Vigorous. Tree growth reaching 1 to 2 meters the first growing season. Growth rate varies with soil type and depth, cultural practices and climatic conditions.

*Form*.—Upright, usually pruned to vase shape.

*Branching habit*.—Upright, crotch angle approximately 30°, a heavy crop load tends to increase branch angles.

*Productivity*.—Productive, produces adequate fruit set annually.

*Bearer*.—Regular, adequate fruit set 7 consecutive years.

*Fertility*.—Self-sterile, pollinator required.

*Density*.—Medium dense, controlled by pruning.

*Hardiness*.—Hardy in all stone fruit growing areas of California. Tree grown in USDA Hardiness Zone 9. Winter chilling requirement is approximately 500 hours at or below 45° F.

Trunk:

*Size*.—Large. Measured 50.8 cm at 30.9 cm above ground on a 12 year old tree. Varies with soil type, climatic conditions and cultural practices.

*Stocky*.—Medium stocky.

*Texture*.—Medium rough, roughness increases with age of tree.

*Color*.—Varies from 7.5YR 3/4 to 7.5YR 3/2.

Branches:

*Size*.—Medium. Average circumference 17.3 cm at 1.2 meters above ground.

*Surface texture*.—New growth relatively smooth. Older growth medium rough, roughness increases with age of growth.

*Lenticels*.—Average number 29 in a 25.8 sq cm area of branch. Average length 4.8 mm. Average width 1.5 mm. Color varies from 7.5YR 7/6 to 7.5YR 6/8.

*Color*.—New growth varies from 7.5YR 4/4 to 2.5GY 6/6. Old growth varies from 2.5YR 2/4 to 5YR 3/2, varies with age of growth.

Leaves:

*Size*.—Large. Average length 160.4 mm. Average width 66.9 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentation over leaf veins, glabrous. Lower surface relatively smooth, slight ridges created by midrib and pinnate venation, glabrous.

*Petiole*.—Average length 33.7 mm. Average width 2.2 mm. Longitudinally grooved. Color varies from 7.5R 2/4 to 2.5GY 6/6. Surface glabrous.

*Glands*.—Shape — reniform. Average length 2.7 mm. Average diameter 1.6 mm. Number varies from 0-2, average number 2. Located primarily on the upper portion of the petiole and the base of the leaf blade. Color varies from 5R 3/8 to 7.5R 2/8.

*Stipules*.—Average number — 2. Average length 11.2 mm. Margin — pectinate. Color varies from 2.5GY 6/6 to 5R 4/8.

*Color*.—Upper surface varies from 5GY 4/8 to 5GY 3/6. Lower surface varies from 5GY 5/4 to 5GY 4/6. Mid-vein color varies from 2.5GY 6/6 to 5GY 7/8.

Flower buds:

*Size*.—Large. Average length 18.2 mm. Average diameter 9.8 mm.

*Hardiness*.—Hardy in all stone fruit growing areas of California.

*Form*.—Conical, becoming elongated before opening.

*Pedicel*.—Average length 17.3 mm. Average width 1.1 mm. Color varies from 5GY 5/6 to 5GY 5/8.

*Color*.—N 9.5/ (white).

*Number of buds per spur*.—Average number 7, varies from 5 to 12.

Flowers:

*Blooming period*.—Date of First Bloom — Feb. 28, 2012. Date of Petal Fall — Mar. 10, 2012, varies slightly with climatic conditions.

*Size*.—Medium to large. Average height 21.0 mm. Average diameter 28.1 mm.

*Petals*.—Size — large. Number — normally 5, alternately arranged to the sepals. Average length 16.7 mm. Average width 15.4 mm. Form — orbicular. Margin — entire. Color — N 9.5/ (white). Both upper and lower surfaces glabrous.

*Sepals*.—Number — normally 5, alternately arranged to the petals. Average length 7.9 mm. Average width 5.2 mm. Form — triangular. Margin — entire. Color — upper surface varies from 5GY 6/6 to 5GY 5/6. Lower surface varies from 7.5R 2/8 to 5GY 4/6. Both upper and lower surfaces glabrous.

*Stamens*.—Average number per flower 36, varies from 35 to 38. Average filament length 12.5 mm. Filament color N 9.5/ (white). Anther color varies from 5Y 8/6 to 5Y 8/8.

*Pollen*.—Self-sterile, pollinator required. Color varies from 2.5Y 7/12 to 2.5Y 6/10.

*Pistil*.—Normally one per flower. Average length 17.1 mm. Stigma height even with the anthers. Color varies from 2.5GY 7/6 to 2.5GY 6/6. Surface — glabrous.

*Fragrance*.—Slight.

*Color*.—N 9.5/ (white).

*Number flowers per flower bud*.—Average 3, varies from 1 to 5.

*Pedicel*.—Average length 22.1 mm. Average width 1.1 mm. Color varies from 5GY 6/6 to 5GY 5/6.

Fruit:

*Maturity when described*.—Firm ripe.

*Date of first picking*.—May 11, 2012.

*Date of last picking*.—May 19, 2012, varies slightly with climatic conditions.

*Size*.—Large. Average diameter axially 26.3 mm. Average transversely in suture plane 23.5 mm. Average weight 10.5 grams, varies slightly with fertility of the soil, amount of thinning and climatic conditions.

*Form*.—Globose to slightly elongated.

*Suture*.—Nearly smooth, extends from base to apex.

*Ventral surface*.—Smooth.

*Apex*.—Slightly retuse.

*Base*.—Slightly retuse.

*Stem cavity*.—Rounded to slightly elongated in suture plane. Average depth 2.0 mm. Average diameter 7.0 mm.

Stem:

*Size*.—Medium. Average length 31.9 mm. Average diameter 1.8 mm.

*Color*.—Varies from 5GY 5/6 to 5GY 4/6.

Flesh:

*Ripens*.—Fairly evenly.

*Texture*.—Firm.

*Fibers*.—Few, small, tender.

*Firmness*.—Firm, comparable to most commercial varieties.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Brix*.—Average Brix 17.9°, varies slightly with amount of fruit per tree and climatic conditions.

*Color*.—Varies from 10YR 9/4 to 2.5Y 8.5/4.

*Pit cavity*.—Average length 13.3 mm. Average width 11.5 mm. Average depth 5.0 mm. Color varies from 2.5Y 8/6 to 7.5R 4/10.

Skin:

*Thickness*.—Medium.

*Surface*.—Smooth.

*Bloom*.—Wanting.

*Tendency to crack*.—None during dry weather. Only a slight tendency to crack in wet weather, varies with the stage of maturity.

*Color*.—Varies from 5R 2/6 to 5R 4/8.

*Tenacity*.—Tenacious to flesh.

*Astringency*.—None.

Stone:

*Type*.—Clingstone.

*Size*.—Medium. Average length 12.3 mm. Average width 10.5 mm. Average thickness 8.1 mm.

*Form*.—Nearly globose.

*Base*.—Flat.

*Apex*.—Rounded.

*Surface*.—Nearly smooth, except for small ridges near the suture.

*Sides*.—Varies from equal to unequal with one side extending further from the suture plane.

*Ridges*.—A small, narrow ridge on each side of suture, extends from base to apex.

*Tendency to split*.—None.

*Color*.—Varies from 10YR 7/6 to 10YR 6/4 when dry.

Kernel:

*Size*.—Small to medium. Average length 7.9 mm. Average width 5.4 mm. Average depth 4.2 mm.

*Form*.—Ovate.

*Viability*.—Partially viable, incomplete embryo in some stones.

*Skin color*.—Varies from 2.5Y 9/4 to 5Y 8.5/2.

Use: Dessert. Market—local and long distance.

Keeping quality: Good, held well for 2 weeks in cold storage at 38° to 42° F. and maintained good appearance and eating quality.

Shipping quality: Good, showed minimal bruising or scarring during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree, substantially as illustrated and described.

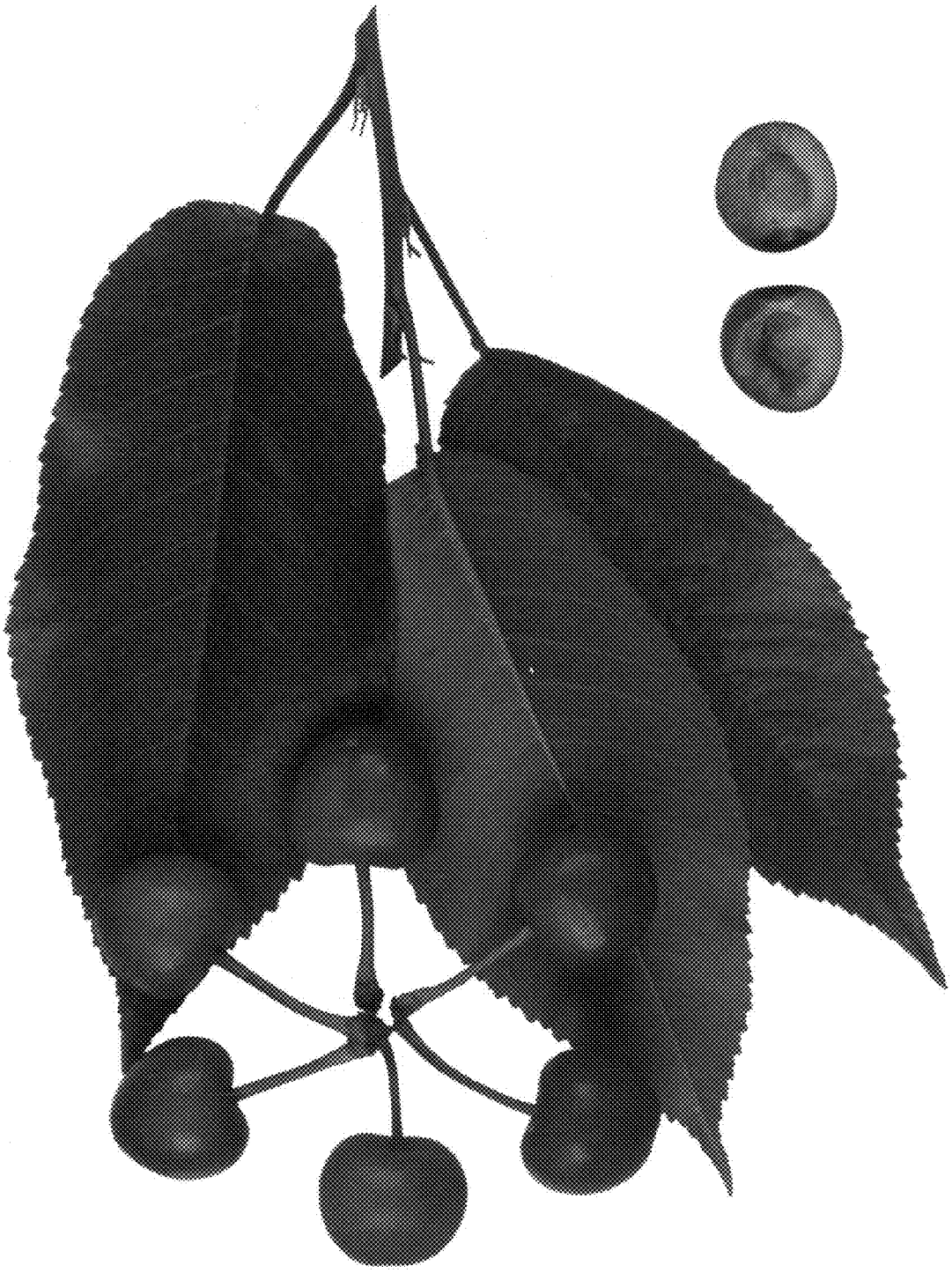

* * * * *